(12) United States Patent
Davis (10) Patent No.: US 11,766,304 B2
(45) Date of Patent: Sep. 26, 2023

(54) STERILE SURGICAL DRAPE FOR USE WITH A C-ARM X-RAY MACHINE

(71) Applicant: Martin Davis, Wilmington, NC (US)

(72) Inventor: Martin Davis, Wilmington, NC (US)

(*) Notice: Subject to any disclaimer, the term of this patent is extended or adjusted under 35 U.S.C. 154(b) by 48 days.

(21) Appl. No.: 17/581,625

(22) Filed: Jan. 21, 2022

(65) Prior Publication Data

US 2023/0062481 A1 Mar. 2, 2023

Related U.S. Application Data

(60) Provisional application No. 63/239,635, filed on Sep. 1, 2021.

(51) Int. Cl.
*A61B 46/10* (2016.01)
*A61B 46/00* (2016.01)
*A61B 90/00* (2016.01)
*A61B 90/40* (2016.01)
*A61B 6/10* (2006.01)
*A61B 6/00* (2006.01)

(52) U.S. Cl.
CPC ............... *A61B 46/10* (2016.02); *A61B 6/10* (2013.01); *A61B 6/4423* (2013.01); *A61B 6/4441* (2013.01); *A61B 46/40* (2016.02); *A61B 90/08* (2016.02); *A61B 90/40* (2016.02)

(58) Field of Classification Search
CPC .... A61B 2046/201; A61B 46/00; A61B 46/10
See application file for complete search history.

(56) References Cited

U.S. PATENT DOCUMENTS

| 2004/0025886 A1* | 2/2004 | Masini | A61B 46/00 128/849 |
| 2016/0166323 A1* | 6/2016 | Tylka | A61B 46/00 128/852 |

* cited by examiner

*Primary Examiner* — Scott Luan
(74) *Attorney, Agent, or Firm* — Ashley D. Johnson; Dogwood Patent and Trademark Law (57) ABSTRACT

The invention is generally directed to a sterile surgical drape designed to provide a sterile barrier with a self-contained, expandable sterile pocket. The sterile surgical drape includes a pocket sized and shaped to accommodate the C-arm of an X-ray machine. The pocket spans the width of the operative site and includes an elastic band along a top edge to ensure that the pocket does not drop below the sterile field when not in use. In this way, the pocket is maintained around the C-arm and the sterile field is preserved during use. The surgical drape can optionally include an adhesive antimicrobial strip configured with an elongated length. The surgical drape can further optionally include one or more pouches sized and shaped to retain surgical instruments or tools.

9 Claims, 7 Drawing Sheets

STERILE SURGICAL DRAPE FOR USE WITH A C-ARM X-RAY MACHINE

CROSS-REFERENCE TO RELATED APPLICATIONS

This application claims priority to U.S. Provisional Patent Application No. 63/239,635 filed Sep. 1, 2021, the entire content of which is hereby incorporated by reference herein.

TECHNICAL FIELD

The presently disclosed subject matter is generally directed to a sterile surgical drape for use with a C-arm of an x-ray machine.

BACKGROUND

X-ray systems are frequently used in surgery to allow health professionals to assess the progress of the surgery and to identify possible complications. Thus, x-rays may be performed multiple times in the course of a single surgery. C-arm systems are commonly used for studies requiring the maximum positional flexibility, such as angiography studies (peripheral, central, and cerebral), therapeutic studies (line placements), cardiac studies (PTCA), and orthopedic procedures (ORIF, DHS, MUA, spinal work). A C-arm system typically comprises several components including a C-arm, table, fluoroscopic exposure and program controls, post processing software, and viewing monitors. The C-arm provides an x-ray source, an arm or C-frame (shaped like a "C" to curve around the table and the patient), and an image intensifier that receives the x-rays and converts them into a visible image.

During surgical procedures, keeping the area sterile is typically accomplished through surgical drapes that isolate the area from the surrounding environment. However, conventional sterile drapes do not account for the movement of the x-ray machine C-arm. As a result, when the C-arm is in use and rotates around the patient, there is a risk that non-sterile portions of the drape can be lifted from the floor into the sterile field (e.g., adjacent to the surgical site). To prevent this from occurring, multiple sterile drapes are typically used to cover the C-arm, which leads to increased waste and unnecessary costs. Therefore, it would be beneficial to provide a sterile surgical drape that accommodates the rotation of a C-arm of an X-ray machine. It would be further beneficial if the drape included one or more utility pockets and/or an extended antimicrobial adhesive strip to accommodate surgical site incisions both proximally and distally on the patient.

SUMMARY

In some embodiments, the presently disclosed subject matter is directed to a surgical drape. Particularly, the drape comprises a body defined by a first drape side and an opposed second drape side. The drape also includes a top edge and opposed bottom edge and a pair of side edges. The drape includes an aperture. The drape also includes a pocket configured on a surface of the first drape side. The pocket is defined by a compartment with an upper edge comprising a retention element (e.g., portion of elastic) and a top face operatively attached to the upper edge of the base. The pocket comprises an outer perimeter that is connected around the aperture of the body.

In some embodiments, the pocket is positioned in an approximate center of the drape body.

In some embodiments, the pocket is offset from an approximate center of the drape body.

In some embodiments, the drape is constructed from cotton, paper, silk, polyethylene, polyester, carbon fiber, ABS plastic, polyurethane rubber, latex, fiver-encased resinous materials, synthetic materials, polymers, natural materials, or combinations thereof.

In some embodiments, the surgical drape further includes an adhesive antimicrobial strip positioned on the first drape side.

In some embodiments, the retention element comprises a portion of elastic material.

In some embodiments, the antimicrobial strip comprises 2,4,4'-arichloro-2'hydroxydiphenyl ether, benzalkonium chloride, silver sulfadiazine, octenidine, polyhexanide (PHMB), triclosan, copper, silver, nanosilver, gold, selenium, gallium, taurolidine, cyclotaurolidine, N-chlorotaurine, alcohol, lauric arginate (LAE), myristamidopropyl dimethlamine (MAPD), povidone iodine, or combinations thereof.

In some embodiments, the antimicrobial is present within the strip at a concentration (w/w) of about 0.01% to about 10.0%.

In some embodiments, the strip comprises one or more additives selected from celecoxib, rofecoxib, aspirin, salicylic acid, acetominophen, indomethicin, sulindac, tolmetin, ketorolac, mefanamic acid, ibuprofen, naproxen, phenylbutazone, sulfinpyrazone, apazone, piroxicam, channel blocking agents, lidocaine, bupivacaine, mepivacaine, procaine, chloroprocaine, ropivacaine, tetracaine, prilocaine, levobupivicaine, rapamycin, growth factors, hylauronic acid, angiogenesis promoting agents, pro-coagulation factors, anti-coagulation factors, chemotactic agents, agents to promote apoptosis, immunomodulators, mitogenic agents, diphenhydramine, chlorpheniramine, pyrilamine, promethazin, meclizine, terfenadine, astemizole, fexofenidine, loratidine, aurothioglucose, auranofin, hydrocortisone, cortisone, fludrocortisone, prednisone, prednisolone, 6α-methylprednisone, triamcinolone, betamethasone, and dexamethasone.

In some embodiments, the surgical drape comprises a length, width, or both of about 4-12 inches.

In some embodiments, the surgical drape further includes at least one pouch configured on the first side of the drape.

In some embodiments, the presently disclosed subject matter is directed to a method of using the C-arm of an x-ray machine within a sterile surgical field. Particularly, the method comprises positioning a sterile surgical drape in an environment to separate the sterile surgical field from a non-sterile field. Particularly, the drape comprises a body defined by a first drape side and an opposed second drape side with an aperture. The drape body also includes a top edge, an opposed bottom edge, and a pair of side edges. The drape also includes a pocket configured in the central portion of the first drape side. The pocket is defined by a compartment with an upper edge comprising a retention element and a top face operatively attached to the upper edge of the base. The pocket comprises an outer perimeter that is connected around the aperture of the body. The method also includes configuring the drape such that the first drape side faces the sterile operating field, and the second drape side faces the non-sterile field. The method comprises advancing the C-arm of the x-ray machine from a non-sterile field through the drape pocket for use within the sterile operating field, wherein the C-arm can be rotated in a lateral position without contaminating the sterile nature of the sterile operating field.

In some embodiments, the presently disclosed subject matter is directed to a kit comprising a plurality of sterile surgical drapes. Particularly, each sterile surgical drape comprises a drape body comprising a first drape side and an opposed second drape side with an aperture. The drape body also includes a top edge, an opposed bottom edge, and a pair of side edges. The drape also includes a pocket configured in the first drape side. The pocket is defined by a compartment with an upper edge comprising a retention element and a top face operatively attached to the upper edge of the base. The pocket comprises an outer perimeter that is connected around the aperture of the body. Each drape also includes a pocket configured in the central portion of the first drape side. The pocket is defined by a base with an upper edge comprising a portion of elastic and a top face operatively attached to the upper edge of the base. The pocket comprises an outer perimeter that is connected around the aperture of the body. Each surgical drape differs from at least one other surgical drape with regard to size, materials use, presence or absence of a microbial strip, presence or absence of a pouch, or combinations thereof. The kit further includes a set of instructions for use.

DETAILED DESCRIPTION

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

As used herein, the term "and/or" includes any and all combinations of one or more of the associated listed items.

Relative terms such as "below" or "above" or "upper" or "lower" or "horizontal" or "vertical" may be used herein to describe a relationship of one element, layer, or region to another element, layer, or region as illustrated in the drawing figures. It will be understood that these terms and those discussed above are intended to encompass different orientations of the device in addition to the orientation depicted in the drawing figures.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

Figure 1:
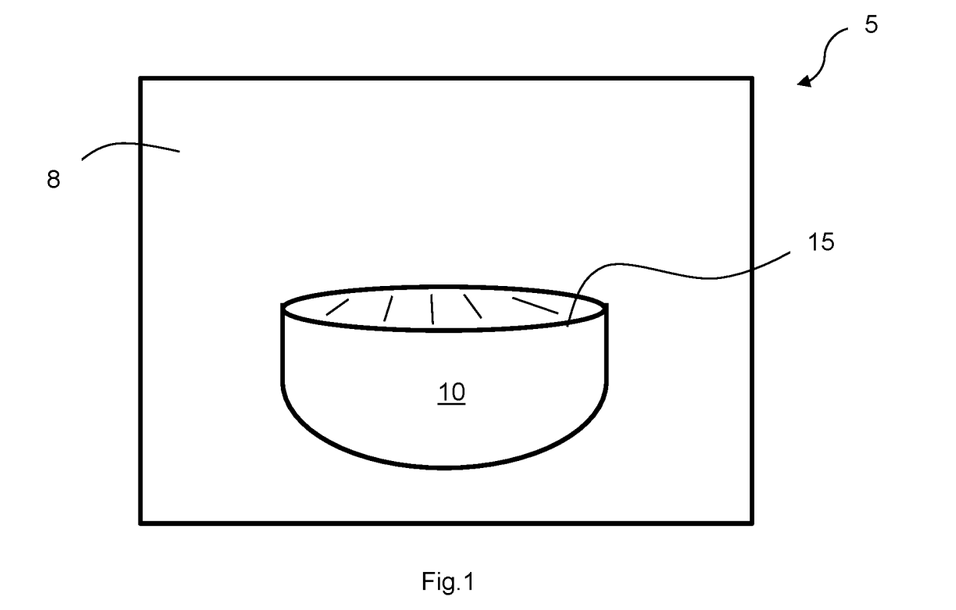
FIG. 1 is a front plan view of a sterile surgical drape in accordance with some embodiments of the presently disclosed subject matter.

The presently disclosed subject matter is generally directed to a sterile surgical drape designed to provide a sterile barrier with a self-contained, expandable sterile pocket. As illustrated in FIG. 1, drape 5 includes body 8 that forms the foundation of the drape, with operably attached pocket 10 sized and shaped to accommodate the C-arm of an X-ray machine. The term "pocket" broadly refers to any sleeve, bag-like receptacle, envelope-like receptacle, holder, or segment sized and shaped to accommodate at least one other item (e.g., the C-arm of an x-ray machine). The pocket spans the width of the patient operative site and includes retention element 15 (e.g., elastic band) along a top edge to ensure that the pocket does not drop below the sterile field when not in use. In this way, pocket 10 is maintained around the C-arm and the sterile field is preserved during rotation of the arm. The patient operative site can include (but is not limited to) the location of a surgical procedure to be performed on a patient (e.g., the location on the patient's body, the physical location of the surgery, and/or the operating room, and surrounding elements).

Figure 2A:
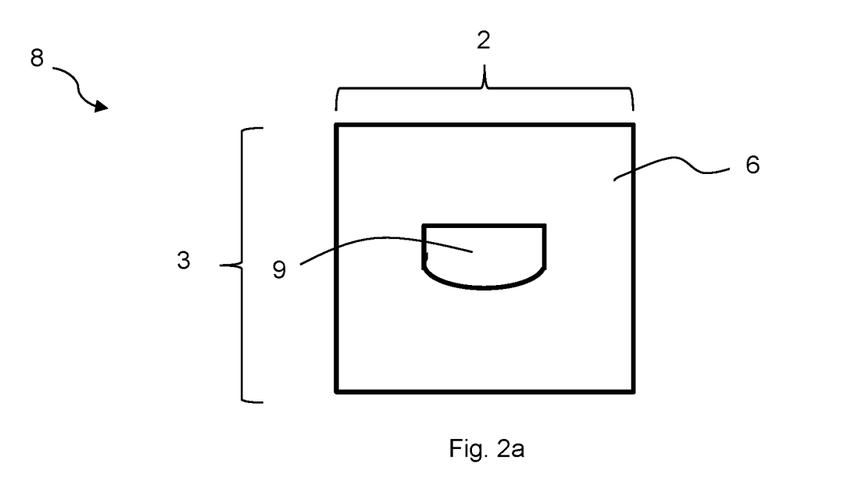
FIG. 2a is a side plan view of the surgical drape of FIG. 1 in accordance with some embodiments of the presently disclosed subject matter.
Figure 2B:
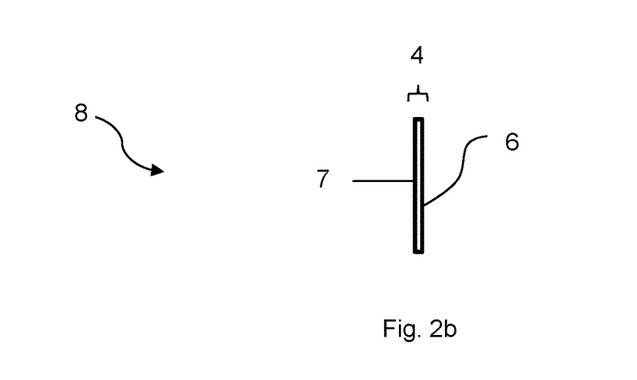
FIG. 2b is a front plan view of a surgical drape in accordance with some embodiments of the presently disclosed subject matter.

The term "drape" refers to the sterile fabric that marks the physical limits of the surgical field. As shown in FIGS. 2a and 2b, drape body 8 includes sterile side 6 and opposed non-sterile side 7. Thus, the sterile drape can define an interface dividing a sterile field and non-sterile field. Only sterile objects and personnel are typically allowed within a sterile field. The term "sterile" refers to a component that meets surgical cleanliness standards and is typically substantially aseptic and/or substantially free from living microorganisms. The term "sterile side" refers to the side of the sterile drape facing the sterile surgical field. The term "non-sterile side" refers to the side of the surgical drape facing the non-sterile surgical field. "Non-sterile" refers to a component that fails to meet surgical cleanliness standards and is typically not aseptic and/or free from living microorganisms.

Figure 3A:
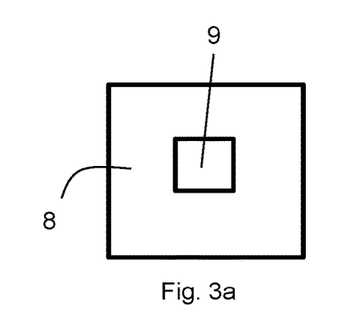
FIGS. 3a-3e are top plan view of surgical drapes in accordance with some embodiments of the presently disclosed subject matter.
Figure 3B:
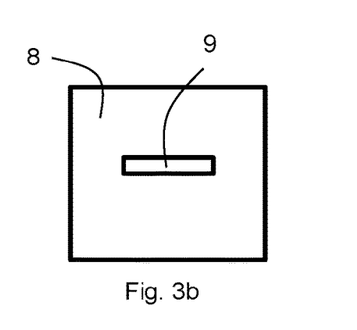
Figure 3C:
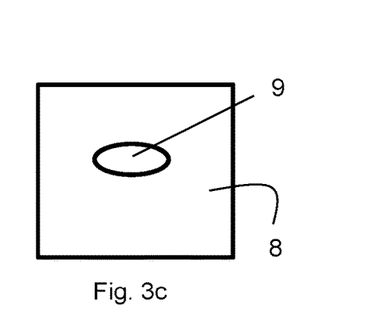
Figure 3D:
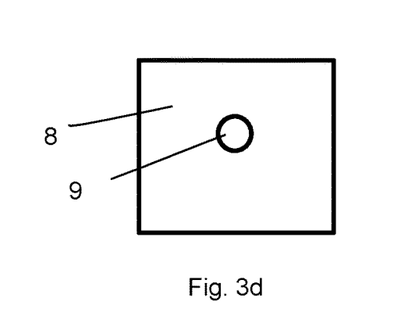
Figure 3E:
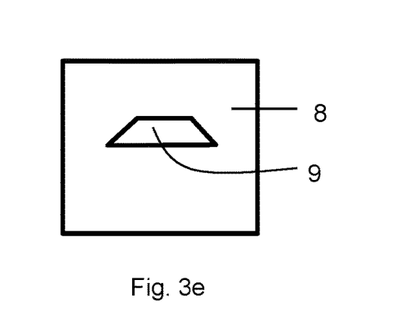
Figure 3F:
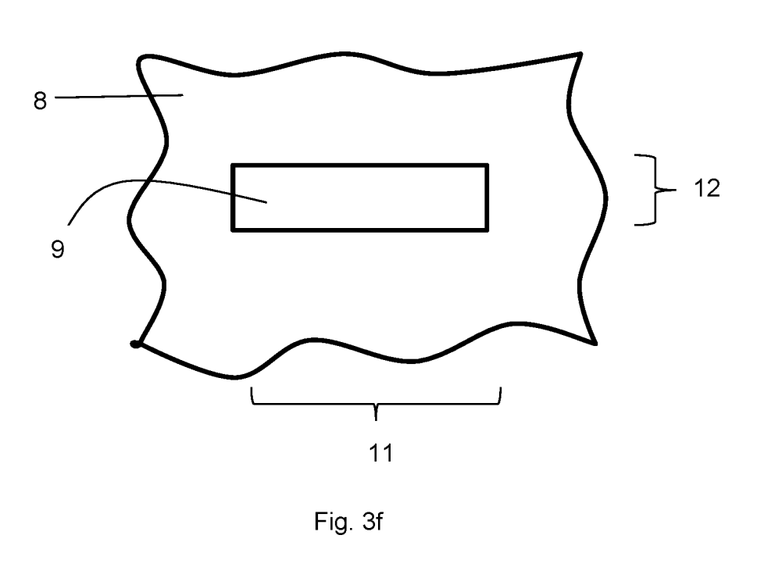
FIG. 3f is a fragmentary top plan view of a surgical drape comprising a pocket in accordance with some embodiments of the presently disclosed subject matter.

The drape body also includes aperture 9 sized and shaped to cooperate with the drape pocket, as illustrated in FIGS. 3a-3e. The term "aperture" refers to any hole, opening, slit, or gap configured through the drape body. Aperture 9 can have any desired size and/or shape (e.g., square, rectangular, oval, round, abstract, and the like as shown in the Figures). In some embodiments, aperture 9 can have length 11 and/or width 12 of about 5-60 inches (e.g., at least/no more than about 5, 10, 15, 20, 25, 30, 35, 40, 45, 50, 55, or 60 inches), as shown in FIG. 3f. The term "length" refers to the longest horizontal straight-line distance of the aperture. The term "width" refers to the longest vertical straight-line distance of the aperture. The aperture can be created using any conventional mechanism, such as the use of a knife, scissors, lasers, cutting tools, and the like.

Drape body 8 can have a squared off and/or rounded shape or portion as illustrated in the embodiment of FIG. 2a. However, the drape can have any desired shape, such as circular, oval, triangular, pentagonal, hexagonal, and the like. Drape body 8 is of sufficient length and width to encompass a human patient and/or an operating table and associated wires, cables, trays, tools, and instruments, including (but not limited to) 3D radiographic equipment, which is used during the course of a sterile surgical procedure. Thus, the drape can have length 2 and/or width 3 of about 10-100 inches (e.g., at least/no more than about 10, 15, 20, 25, 30, 35, 40, 45, 50, 55, 60, 65, 70, 75, 80, 85, 90, 95, or 100 inches). The term "length" refers to the longest horizontal straight-line distance of the drape (e.g., from a first side edge to the opposed second side edge). The term "width" refers the longest vertical straight-line distance of the drape (e.g., the from the top edge to the bottom edge). However, it should be appreciated that the length and width of drape 5 are not limited and can be configured outside the ranges given above.

The surgical drape body can have any suitable thickness 4, such as (but not limited to) about 0.001-0.1 inches. Thus, body 8 can have a thickness of about 0.001, 0.005, 0.01, 0.05, or 0.1 inches in some embodiments. The term "thickness" refers to the distance between the opposing sides of the drape body (e.g., sides 6 and 7).

Figure 4A:
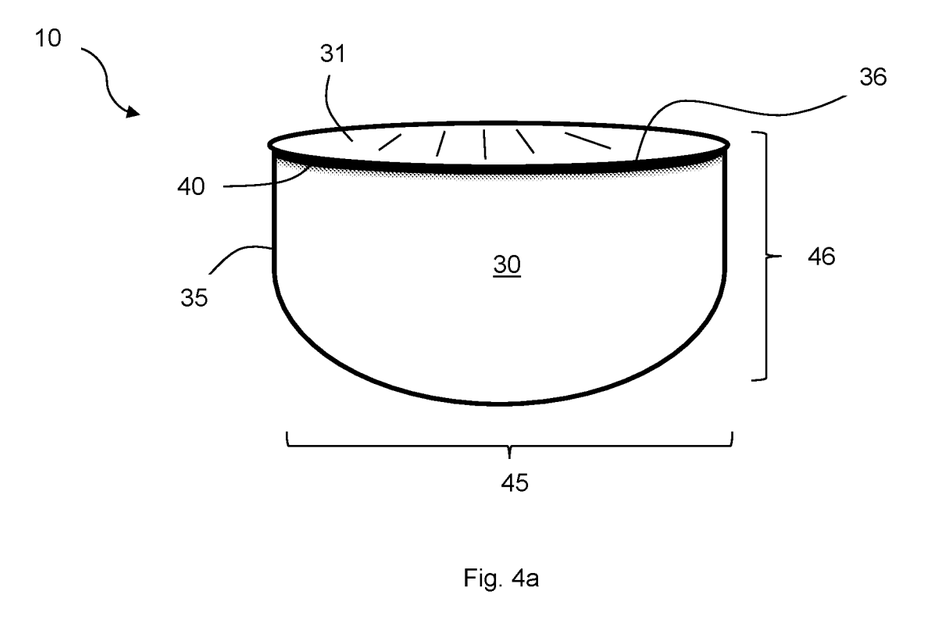
FIG. 4a is a perspective view of a drape pocket in accordance with some embodiments of the presently disclosed subject matter.

As set forth above, drape body 8 is configured as a flexible covering with sterile side 6. The sterile side includes pocket 10 that is at least partially conformable to the C-arm of an X-ray machine. As shown in FIG. 4a, pocket 10 includes compartment 30 and top face 31 with a size and shape configured to house the C-arm. In some embodiments, the top face is substantially flat and/or horizontal compared to the compartment. The compartment includes outer edge 35 that is attached using conventional mechanisms around the exterior of body aperture 9. For example, sewing, adhesives, thermoforming, and other similar techniques can be used. In some embodiments, the perimeter of the pocket is configured in about the same shape as aperture 9. The compartment includes upper edge 36 about which top face 31 is attached using sewing, adhesives, thermoforming, or any other mechanism. The top face and compartment therefore create a pocket to house the C-arm. Upper edge 36 can also include retention element 40 to assist in maintaining the shape of the pocket when not in use (e.g., keeping the drape from contacting the floor). In some embodiments, the retention element can be configured as a portion of elastic. The term "elastic" can include any material that can stretch and return to its original length after the stretching force is removed. The retention element can be configured as any element that can maintain the shape of the pocket when not in use (and to ensure that the pocket does not fall on the floor), such as the use of magnets, VELCRO®, ties, clips, fasteners, buttons, snaps, cords, cordage, self-adhesive, and the like.

The pocket compartment can have a generally square, rectangular, or rounded shape. It should further be appreciated that any shape can be used so long as it is capable of housing the C-arm of an x-ray machine.

Figure 4B:
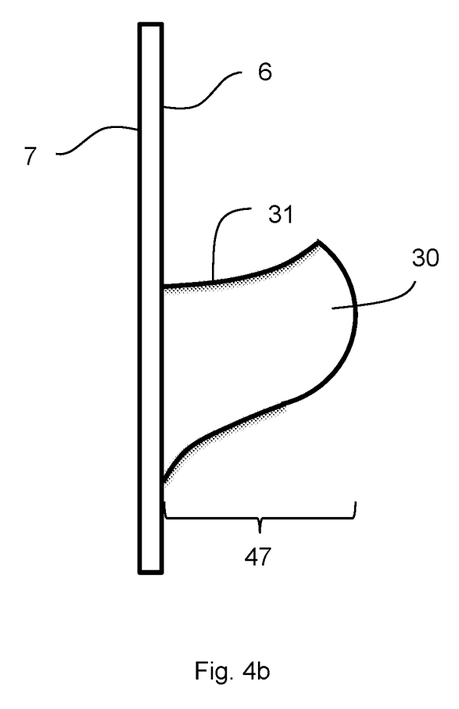
FIG. 4b is a side plan view of a pocket configured on a surgical drape in accordance with some embodiments of the presently disclosed subject matter.
Figure 5A:
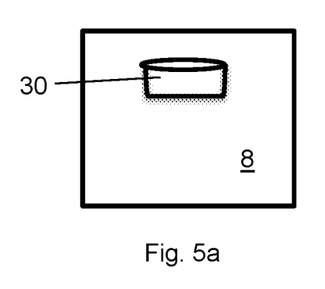
FIG. 5a-5d are top plan views of a surgical drape comprising an off-centered pocket in accordance with some embodiments of the presently disclosed subject matter.
Figure 5B:
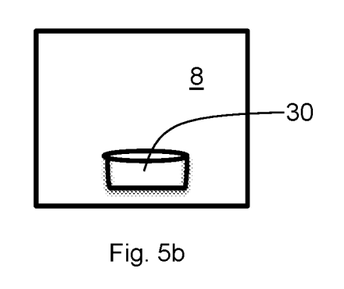
Figure 5C:
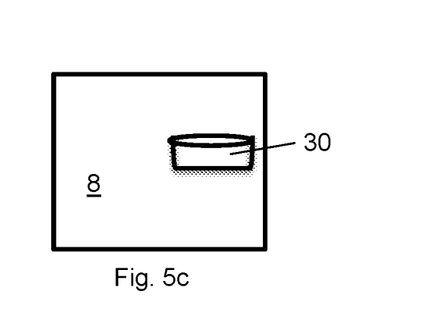
Figure 5D:
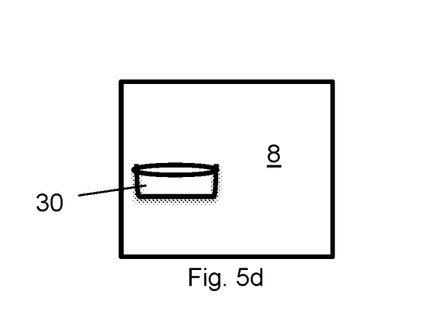

Pocket 10 includes length 45 and width 46. The length and/or width of the pocket can be about 10-70 inches (e.g., at least/no more than about 10, 15, 20, 25, 30, 35, 40, 45, 50, 55, 60, 65, or 70 inches). However, the presently disclosed subject matter is not limited and the size of pocket 10 can vary widely. The pocket can also include thickness 47, as shown in FIG. 4b. The term "thickness" refers to the longest horizontal distance extending from the drape when in use.

In some embodiments, the pocket can be positioned in the approximate center portion of drape 5. However, pocket 10 can be configured on any surface of drape body 8, such as off centered, toward the right or left side of the drape, or toward the top or bottom of the drape, as shown in FIGS. 5a-5d. It should be appreciated that the location of the surgical site relative to C-arm may be beneficial if positioned off center from the drape center point. For example, the location may make it easier to access the operative site, may make it easier for the doctor to perform a desired function, and/or may make it easier for the C-arm to be properly positioned relative to the operative site.

Figure 6:
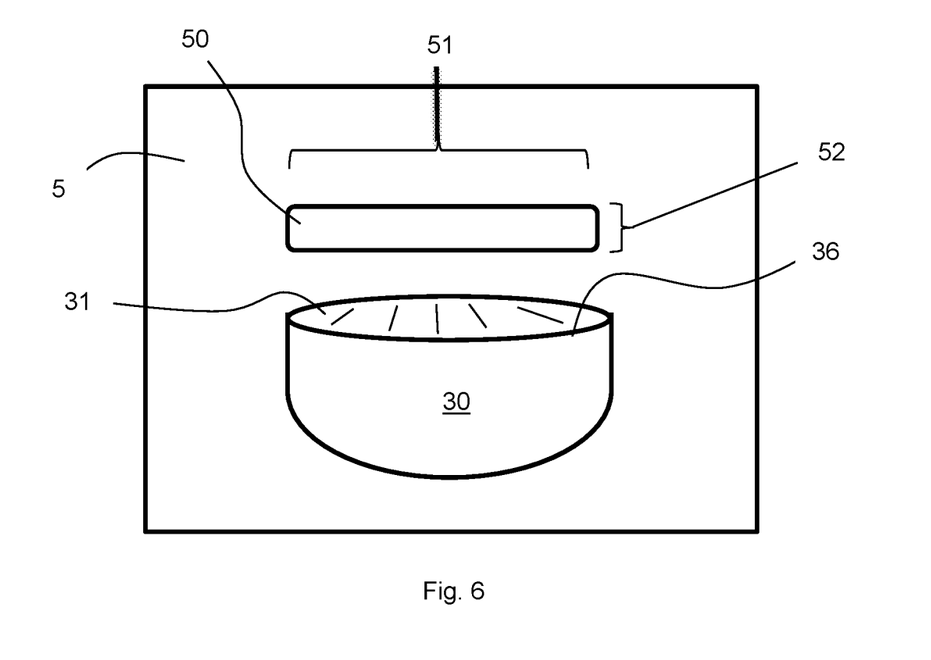
FIG. 6 is a front plan view of a surgical drape comprising an antimicrobial strip in accordance with some embodiments of the presently disclosed subject matter.

In some embodiments, drape 5 includes strip 50 to accommodate surgical site incisions both proximally and distally on the patient, as shown in FIG. 6. The strip can comprise adhesive on at least one surface and at least one antimicrobial agent. Any suitable adhesive can be used, such as (but not limited to) an acrylate adhesive. In use, the practitioner places the strip on the skin of the patient using the adhesive surface to adhere the strip to the skin. The antimicrobial surface is then in direct contact with the wound site.

In some embodiments, the strip (e.g., the adhesive layer) includes at least one antimicrobial agent to inhibit the growth of microorganisms on the skin of the patient adjacent to the adhesive. The term "antimicrobial" refers to an ability to kill or inhibit the growth of microorganisms, including (but not limited to) bacteria, viruses, yeast, fungi, and protozoa, or to attenuate the severity of a microbial infection.

Suitable antimicrobial agents include (but are not limited to) 2,4,4'-arichloro-2'hydroxydiphenyl ether, benzalkonium chloride, silver sulfadiazine, octenidine, polyhexanide (PHMB), triclosan, copper, silver, nanosilver, gold, selenium, gallium, taurolidine, cyclotaurolidine, N-chlorotaurine, alcohol, lauric arginate (LAE), myristamidopropyl dimethylamine (MAPD), OAPD and/or povidone iodine. The antimicrobial agent can be present within the adhesive layer at a concentration (w/w) of about 0.01% to about 10.0% of the adhesive (e.g., at least/no more than about 0.01, 0.1, 0.5, 1, 1.5, 2, 2.5, 3, 3.5, 4, 4.5, 5, 5.5, 6, 6.5, 7, 7.5, 8, 8.5, 9, 9.5, or 10%).

Any therapeutic agent or desired additive can be incorporated into strip 50. Examples of such therapeutic agents or additives include (but are not limited to) anti-inflammatory agents (such as celecoxib, rofecoxib, aspirin, salicylic acid, acetominophen, indomethicin, sulindac, tolmetin, ketorolac, mefenamic acid, ibuprofen, naproxen, phenylbutazone, sulfinpyrazone, apazone, piroxicam), anesthetic agents (channel blocking agents, lidocaine, bupivacaine, mepivacaine, procaine, chloroprocaine, ropivacaine, tetracaine, prilocaine, levobupivicaine, and combinations of local anesthetics with epinephrine, etc.), anti-proliferatives (rapamycin, etc.), growth factors (PGDF, etc.), scar treatment agents (hylauronic acid), angio-genesis promoting agents, pro-coagulation factors, anti-coagulation factors, chemotactic agents, agents to promote apoptosis, immunomodulators, mitogenic agents, diphenhydramine, chlorpheniramine, pyrilamine, promethazin, meclizine, terfenadine, astemizole, fexofenidine, loratidine, aurothioglucose, auranofin, Cortisol (hydrocortisone), cortisone, fludrocortisone, prednisone, prednisolone, 6α-methylprednisone, triamcinolone, betamethasone, and dexamethasone. Each additive can be present in the strip in an amount of from about 0.01% to about 10.0% of the adhesive (e.g., at least/no more than about 0.01, 0.1, 0.5, 1, 1.5, 2, 2.5, 3, 3.5, 4, 4.5, 5, 5.5, 6, 6.5, 7, 7.5, 8, 8.5, 9, 9.5, or 10%). However, the additives are optional.

Under normal conditions, the strip is retained over the healing surgical incision for about 5-7 days, substantially preventing dehiscence of the incision and allowing healing.

Strip 50 can be rectangular in shape, as shown in FIG. 6. However, the strip can have any desired shape. Further, the strip can include length 51 and/or width 52 of about 4-12 inches (e.g., at least/no more than about 4, 5, 6, 7, 8, 9, 10, 11, or 12 inches). However, the strip can be prepared in a variety of sizes and shapes for particular applications, including a variety of surgery procedures. Advantageously, strip 50 is of a size applicable for a wide variety of surgical wounds such that only a single strip is needed.

It should be appreciated that strip 50 is optional, and the disclosed drape can be configured without the strip in some embodiments.

Figure 7A:
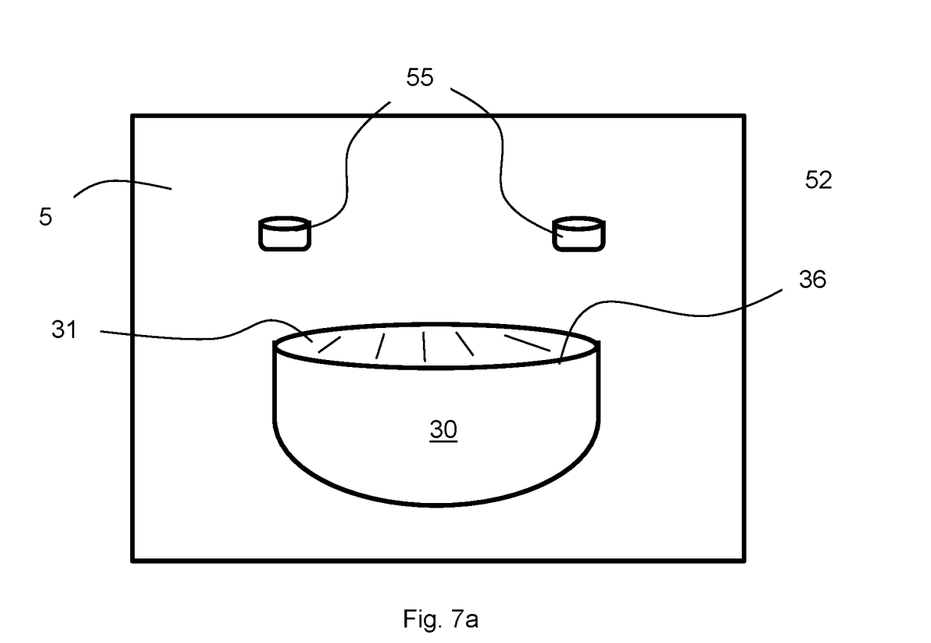
FIG. 7a is a front plan view of a surgical drape comprising a pair of pouches in accordance with some embodiments of the presently disclosed subject matter.
Figure 7B:
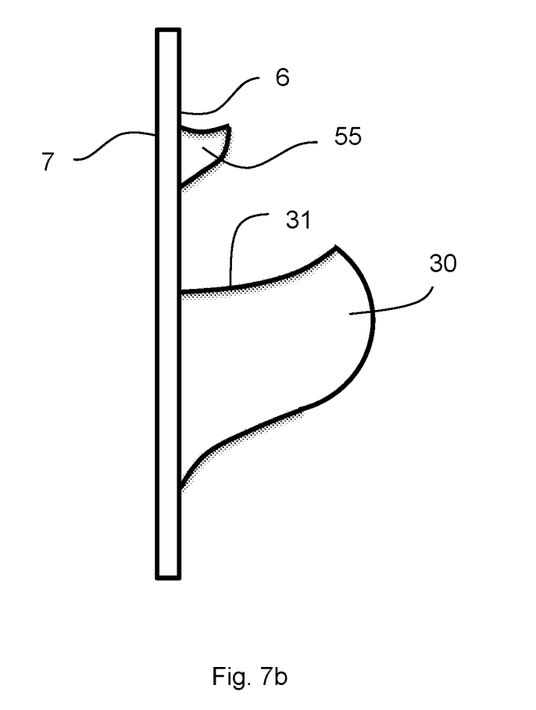
FIG. 7b is a side plan view of the surgical drape of FIG. 7a in accordance with some embodiments of the presently disclosed subject matter.

In some embodiments, drape 5 can include one or more optional pouches 55 that can be used to store one or more items, as shown in FIGS. 7a and 7b. For example, surgical instruments can be stored in pouch 55 to ensure that they do not interfere with operative care. Fluid waste can be drained from the extendable pouch or collected within an enclosure along the bottom of the drape. The term "pouch" refers to any enclosure, receptacle, or container capable of receiving and retaining at least one item.

Each pouch can have any desired dimensions to house a wide variety of instruments. Further, the drape can include any number of pouches, such as about 1-10 (e.g., 1, 2, 3, 4, 5, 6, 7, 8, 9, or 10). In some embodiments, each pouch can be configured in about the same size and/or shape. In other embodiments, at least one pouch 55 differs from at least one other pouch with respect to size and/or shape.

Drape body 8 and pocket 10 can be constructed from any of a wide variety of suitable materials, such as (but not limited to) cotton, paper, silk, polyethylene, polyester, carbon fiber, ABS plastic, polyurethane rubber, latex, silicone, fiber-encased resinous materials, synthetic materials, polymers, natural materials, or combinations thereof.

In some embodiments, the disclosed drape body and/or pocket are opaque to reduce the incidence of outside distractions to the medical staff and/or provide privacy to the patient within the surgical field. The term "opaque" refers to the optical state of a medium with transmittance of less than about 2% of the incident visible light. However, the presently disclosed subject matter also includes embodiments wherein the drape is transparent or semi-transparent. The term "transparent" refers to a material that has the property of transmitting visible light without appreciable scattering such that an object placed beyond the transparent material is visible (e.g., a transmittance of 80% or more). The term "semi-transparent" refers to a material that has the property of transmitting visible light with some appreciable scattering, such that an object placed beyond the semi-transparent material is at least partially visible (e.g., transmittance of between about 2-80%).

Figure 8A:
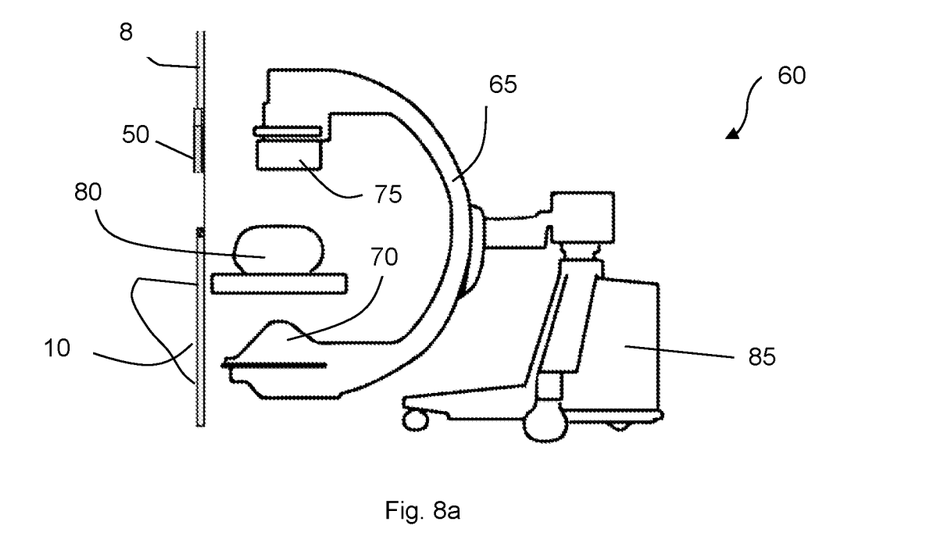
FIG. 8a is a side plan view of a C-arm x-ray machine in use with a patient in accordance with some embodiments of the presently disclosed subject matter.
Figure 8B:
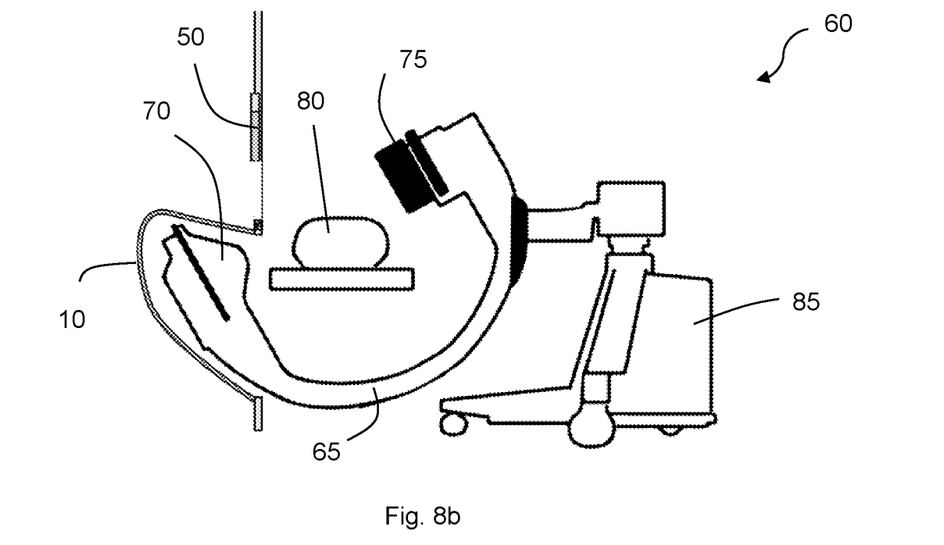
FIG. 8b is a perspective view of a drape configured for use with the C-arm of an x-ray machine in accordance with some embodiments of the presently disclosed subject matter.

In use, drape 5 can be used with the C-arm of an x-ray machine. FIG. 8a illustrates a representative C-Arm X-ray/irradiation system 60 in which C-arm 65 comprises x-ray or radiation source 70 and detector 75 configured to irradiate patient 80 and provide image information to processor 85 for analysis. The drape can be hung conventionally, and the C-arm is housed within pocket 10, as shown in FIG. 8b. Specifically, the pocket spans the width of the operative site, with the retention element (e.g., elastic band) ensuring that the pocket does not drop below the sterile field when not in use. The pocket therefore creates an expandable sterile barrier in the middle of drape 5 to accommodate the C-arm x-ray machine in the lateral position.

If desired, antimicrobial strip 50 can be used directly with a surgical site incision both proximally and distally on patient 80. The term "proximally" refers to the direction opposite to the direction of blood flow or upstream from the direction of blood flow. The term "distally" refers to a location that is downstream in the direction of blood flow. As set forth in detail above, the strip can include one or more antimicrobial materials to help prevent infection and/or promote healing.

In some embodiments, one or more surgical tools can be housed within pouch 55 to keep the items convenient for use, yet out of the way when not needed.

The current utility pouches are aligned with the surgical site, which interferes with operative care. When this occurs, there is a high probability for the drape to be compromised from tearing.

The presently disclosed subject matter includes many advantages over prior art drapes. Specifically, drape 5 has been designed to improve patient care through sterility and cost effectiveness.

Pocket 10 prevents the non-sterile portions of the drape from being lifted from the floor into the sterile field. Thus, the pocket is configured to house the C-arm of an x-ray machine during use. Accordingly, the risk of infection is decreased due a lack of movement of non-sterile areas within the sterile field.

The disclosed drape decreases or eliminates the need for extra sterile drapes to be used. As a result, waste is reduced and there is a cost savings for the hospital and patient. Because the extra drapes are not needed, time is also saved. For example, when extra drapes are used, a new drape must be added each time a lateral view of the C-arm is needed, which can be 10-20 times in a single use.

Antimicrobial strip 50 is configured to be long enough to cover the distal surgical site. Thus, a single strip can be used on a patient instead of multiple strips as conventionally done.

The foregoing descriptions have been presented for purposes of illustration and description and are not intended to be exhaustive or to limit the presently disclosed subject matter. Many modifications and variations are possible in light of the present disclosure.

What is claimed is:

1. A method of using a C-arm of an x-ray machine within a sterile surgical field, the method comprising:
   positioning a sterile surgical drape in an environment to separate the sterile surgical field from a non-sterile field, wherein the sterile surgical drape is defined by:
   a drape body comprising a first drape side, an opposed second drape side, an aperture defined by an exterior edge, wherein the drape body comprises a top edge, opposed bottom edge, and a pair of side edges;
   a collapsible pocket configured in the central portion of the first drape side, the pocket defined by:
   an opening compartment with a volume defined by a base that includes an upper edge comprising a retention element, and a substantially horizontal top face defined by a first edge and a second edge, wherein the first edge abuts and attaches to the exterior edge of the aperture, and the second edge is operatively attached to the upper edge of the base;
   wherein the pocket comprises an outer perimeter that is connected around the aperture of the body;
   configuring the drape such that the first drape side faces the sterile operating field, and the second drape side faces the non-sterile field; and
   advancing the C-arm of the x-ray machine within the sterile operating field through the drape pocket opening compartment, wherein the C-arm can be rotated in a lateral position without contaminating the sterile nature of the sterile operating field; and
   wherein when the C-arm is rotated in the lateral position, the collapsible pocket allows the C-arm to extend to increase the volume of the sterile surgical field;
   wherein the retention element maintains the pocket in a non-use shape when the C-arm is retracted; and
   wherein in the non-use shape, the pocket is not touching the non-sterile ground.

2. The method of claim 1, wherein the surgical drape is constructed from cotton, paper, silk, polyethylene, polyester, carbon fiber, ABS plastic, polyurethane rubber, latex, fiver-encased resinous materials, synthetic materials, polymers, natural materials, or combinations thereof.

3. The method of claim 1, wherein the surgical drape further comprises an adhesive antimicrobial strip positioned on the first drape side.

4. The method of claim 3, wherein the antimicrobial strip comprises 2,4,4'-arichloro-2'hydroxydiphenyl ether, benzalkonium chloride, silver sulfadiazine, octenidine, polyhexanide (PHMB), triclosan, copper, silver, nanosilver, gold, selenium, gallium, taurolidine, cyclotaurolidine, N-chlorotaurine, alcohol, lauric arginate (LAE), myristamidopropyl dimethlamine (MAPD), povidone iodine, or combinations thereof with a concentration of about 0.01 weight % to about 10.0 weight %, based on the total weight of the strip.

5. The method of claim 1, wherein the surgical drape further comprises at least one pouch positioned on the first drape side.

6. The method of claim 1, wherein the surgical drape pocket is positioned in an approximate center of the drape body.

7. The method of claim 1, wherein the surgical drape pocket is offset from an approximate center of the drape body.

8. The method of claim 1, wherein the surgical drape pocket has a length, width, or both of about 10-70 inches.

9. The method of claim 1, wherein the retention element comprises a portion of elastic material.

\* \* \* \* \*